United States Patent
Stegman

(10) Patent No.: US 11,547,813 B2
(45) Date of Patent: Jan. 10, 2023

(54) AEROSOL MEDICAMENT DELIVERY ADAPTER AND SYSTEM FOR DISPENSING MEDICAMENT INTO A VENTILATION CIRCUIT

(71) Applicant: KONINKLIJKE PHILIPS N.V., Eindhoven (NL)

(72) Inventor: Steven Charles Stegman, Gibsonia, PA (US)

(73) Assignee: Koninklijke Philips N.V., Eindhoven (NL)

( * ) Notice: Subject to any disclaimer, the term of this patent is extended or adjusted under 35 U.S.C. 154(b) by 580 days.

(21) Appl. No.: 16/628,938

(22) PCT Filed: Jun. 29, 2018

(86) PCT No.: PCT/EP2018/067512
§ 371 (c)(1),
(2) Date: Jan. 6, 2020

(87) PCT Pub. No.: WO2019/007818
PCT Pub. Date: Jan. 10, 2019

(65) Prior Publication Data
US 2020/0215274 A1    Jul. 9, 2020

Related U.S. Application Data

(60) Provisional application No. 62/623,663, filed on Jan. 30, 2018, provisional application No. 62/529,501, filed on Jul. 7, 2017.

(51) Int. Cl.
*A61M 11/00* (2006.01)
*A61M 16/08* (2006.01)

(52) U.S. Cl.
CPC ......... *A61M 11/006* (2014.02); *A61M 11/002* (2014.02); *A61M 16/0833* (2014.02); *A61M 2206/10* (2013.01)

(58) Field of Classification Search
CPC ........ A61M 16/08–0891; A61M 11/02; A61M 11/006; A61M 2206/10
See application file for complete search history.

(56) References Cited

U.S. PATENT DOCUMENTS 8,944,050 B2   2/2015   Hyun et al.
9,155,849 B2   10/2015  Haroutunian
(Continued)

FOREIGN PATENT DOCUMENTS

DE   19807682 A1    8/1999
WO   2014109749 A1  7/2014

OTHER PUBLICATIONS

International Search Report—PCT/EP2018/067512 dated Jun. 29, 2018.

*Primary Examiner* — Valerie L Woodward
(74) *Attorney, Agent, or Firm* — Daniel H. Brean

(57) ABSTRACT

An aerosol medicament delivery adapter comprises a first conduit, second conduit and a diverter element. The first conduit encloses a flow path chamber and extends between an upstream first end and a downstream second end. The second conduit comprises an aerosol medicament delivery conduit that includes an upstream first end adapted to be fluidly coupled to a particle generator, and a downstream second end luidly coupled to the first conduit at a Y-junction proximate the upstream first end of the first conduit. The diverter element comprises a flow diverter chamber disposed within the first conduit or the second conduit. The cylindrical flow diverter chamber includes a transitional flow cross-section and a principal axis, extending between a first end and a second end thereof. The diverter element creates flow eddies for enhancing an entrainment of aerosol particles, delivered via the second conduit, within a pressurized gas flow along the flow path within the first conduit.

15 Claims, 7 Drawing Sheets

(56) References Cited

U.S. PATENT DOCUMENTS

| | | |
|---|---|---|
| 9,216,259 B2 | 12/2015 | Kakade |
| 9,604,018 B2 | 3/2017 | Gallem et al. |
| 2002/0002975 A1* | 1/2002 | Power ............... A61M 16/0833 |
| | | 128/203.12 |
| 2005/0139211 A1* | 6/2005 | Alston ................ A61M 16/204 |
| | | 128/205.24 |
| 2006/0120968 A1 | 6/2006 | Brown et al. |
| 2007/0083677 A1* | 4/2007 | Cecka ............... A61M 16/0841 |
| | | 710/1 |
| 2011/0230820 A1* | 9/2011 | Lillis .................... A61M 13/00 |
| | | 604/24 |

* cited by examiner

AEROSOL MEDICAMENT DELIVERY ADAPTER AND SYSTEM FOR DISPENSING MEDICAMENT INTO A VENTILATION CIRCUIT

CROSS-REFERENCE TO PRIOR APPLICATIONS

This application claims the priority benefit under 35 U.S.C. § 371 of International Patent Application No. PCT/EP2018/067512, filed on Jun. 29, 2018, which claims the priority benefit of U.S. Provisional Patent Application Nos. 62/623,663 and 62/529,501, filed on Jan. 30, 2018 and Jul. 7, 2017, the contents of which are herein incorporated by reference.

The present embodiments relate generally to patient ventilation circuits and more particularly, to an aerosol medicament delivery adapter and system for dispensing medicament into a patient ventilation circuit.

A patient in need of Non Invasive or PAP therapy needs to wear a mask designed for that application. At times, the patient may require nebulized medication to improve their condition. The key to effective aerosolized medication delivery in a gas path is getting the aerosolized medicine particles from the particle generator, thru the gas path and into the patient's lungs. Due to the many opportunities for the medicine particles to come into contact with any of the gas path surfaces, the efficiency of medicine delivery is not very good, (<20% typical).

Inhaled medications can be expensive and caustic. It would be desirable to increase an efficiency of medicine delivery to a patient and thereby reduce an amount of medicine required to support the patient receiving inhaled medications.

Accordingly, an improved method and apparatus for improving an efficiency of aerosolized medicine delivery and overcoming the problems in the art is desired.

In accordance with one aspect, a diverter element of a custom shape is introduced in an otherwise standard flow cross-section. The diverter element is configured to alter a flow path to accomplish a specific task of picking up or entraining aerosolized medication from a particle generator and to efficiently carry the entrained particles along a gas flow path. The diverter element advantageously increases an entrainment of particles downstream of the particle generator by introducing a specific geometry into the airflow path that creates unique flow patterns that divert into the particle reservoir, entrain the particles, and re-enter the main air stream. In addition, by changing the size, shape and orientation of the specific geometry, the entrainment efficiency can be tuned across a wide range of flow rates.

In accordance with another aspect, a flow path upstream of a particle generator exit is customized via a diverter element. As a result, flow eddies are created that effectively pick up or entrain an increased quantity of medicine particles to then be conveyed along a gas path of a patient ventilation circuit. In one embodiment, the diverter element customizations take the form of designed "bumps" extending from the wall of a gas path component, strategically sized, shaped, and located just upstream of the particle generator.

By introducing more aerosolized medicine into the gas path, more medicine is potentially introduced into the patient's lungs. Advantageously, this can allow for a reduction in dosage, thereby further advantageously reducing the time and cost of the application of the aerosolized medicine to the patient. As noted herein above, inhaled medications can be expensive and caustic. By increasing the efficiency of the aerosolized medicine delivery, the amount of aerosolized medicine required to support the patient can advantageously be reduced.

In accordance with another aspect, the embodiments of the present disclosure include a custom design feature (i.e., a flow modifying feature) in the gas path that generates the required change in flow behaviour from the standard design to induce the desired change in particle utilization (i.e., entrainment of particles). The designed flow path flow characteristics are analysed using a computational fluid dynamics (CFD) software program. Once the results are analysed, a flow modifying feature is introduced to change the flow behaviour. This feature (i.e., the flow modifying feature) addition is then analysed using the CFD program and the results are compared to a baseline.

According to one embodiment, an aerosol medicament delivery adapter comprises a first conduit, a second conduit and a diverter element. The first conduit comprises a flow path conduit enclosing a cylindrical flow path chamber having (i) a first radial cross-sectional dimension and (ii) a first principal axis, extending between a first end that corresponds to an upstream end and a second end that corresponds to a downstream end. The second conduit comprises an aerosol medicament delivery conduit enclosing a cylindrical aerosol delivery chamber having (i) a second radial cross-sectional dimension and (ii) a second principal axis, extending between a first end that corresponds to an upstream end and a second end that corresponds to a downstream end of the second conduit. The first end of the second conduit is adapted to be fluidly coupled to a nebulizer or particle generator, and the second end of the second conduit is fluidly coupled to the first conduit at a Y-junction proximate the first end of the first conduit.

The diverter element comprises a cylindrical flow diverter chamber disposed within at least one of the first conduit and the second conduit. The cylindrical flow diverter chamber includes (a)(i) a transitional flow cross-section and (a)(ii) a third principal axis, extending between a first end and a second end of the cylindrical flow diverter chamber. The transitional flow cross-section of the cylindrical flow diverter chamber includes a flow path cross-section perpendicular to the third principal axis that transitions from (b)(i) a first cross-section of a third radial cross-sectional dimension at the first end of the cylindrical flow diverter chamber to (b)(ii) a second cross-section that comprises a compound cross-section that includes a first portion with the third radial cross-section dimension and a second portion with a cross-sectional dimension determined by a flow diverter transition surface at the second end of the cylindrical flow diverter chamber.

The second end of the cylindrical flow diverter chamber is fluidly coupled (c)(i) within the first conduit proximate the first end of the first conduit, upstream of the second conduit or (c)(ii) within the second conduit downstream of the nebulizer or particle generator at, or proximate to, the Y-junction, wherein responsive to a pressurized gas flow along a flow path within the first conduit in a downstream direction. The diverter element creates flow eddies for enhancing an entrainment of aerosol particles, delivered via the second conduit, within the pressurized gas flow along the flow path within the first conduit.

In another embodiment, the aerosol medicament delivery adapter further includes wherein the second cross-section at the second end of the cylindrical flow diverter chamber comprises a semi-circular cross-section. In addition, the first portion includes the partial third radial cross-sectional dimension. Furthermore, the second portion includes a flat portion determined by the flow diverter transition surface. Still further, the transitional flow cross-section at the second end of the cylindrical flow diverter chamber comprises one selected from the group consisting of (i) a small diverter that corresponds with the semi-circular cross-section at the second end of the cylindrical flow diverter chamber being at least 90% of a circular cross-section at the first end of the cylindrical flow diverter chamber, (ii) a medium diverter that corresponds with the semi-circular cross-section at the second end of the cylindrical flow diverter chamber being at least 75%, but less than 90% of the circular cross-section at the first end of the cylindrical flow diverter chamber, and (iii) a large diverter that corresponds with the semi-circular cross-section at the second end of the cylindrical flow diverter chamber being at least 50%, but less than 75%, of the circular cross-section at the first end of the cylindrical flow diverter chamber.

According to another embodiment, the aerosol medicament delivery adapter includes wherein the first principal axis and the second principal axis are disposed in a plane, and wherein the second portion of the compound cross-section is one selected from the group consisting of (a) oriented at an angle parallel to the plane and (b) rotated out of parallel with the plane at an angle within a range of −90 to +90 degrees with respect to the plane. In one embodiment, the aerosol medicament delivery adapter further includes wherein the cylindrical flow diverter chamber is rotatable about the third principal axis for disposing the second portion of the compound cross-section in one or more angles within the range of −90 to +90 degrees with respect to the plane.

According to yet another embodiment, the aerosol medicament delivery adapter further includes wherein the third principal axis is aligned with one selected from the group consisting of the first principal axis and the second principal axis. In another embodiment, the second end of the cylindrical flow diverter chamber is located upstream within the first conduit, and further wherein the second end of the cylindrical flow diverter chamber is spaced by a distance of up to 20 mm from a position within the first conduit where the second conduit intersects with the first conduit. In another embodiment, the first conduit, second conduit and diverter element are integrally formed with one another. In addition, the transitional flow cross-section can include a non-linear transition.

In another embodiment, the Y-junction comprises the second conduit (or aerosol delivery conduit) being coupled to the first conduit (or flow path conduit) such that the second principal axis intersects the first principal axis at an angle of less than 90 degrees. In a further embodiment, the second principal axis is angled with respect to the first principal axis for enabling the second conduit to have a downstream flow direction of aerosolized delivery that opposes the downstream direction of the pressurized gas flow.

In another embodiment, the second end of the aerosol delivery conduit is coupled to the flow path conduit nearer to the first end of the flow path conduit than to the second end of the flow path conduit. In yet another embodiment, the transitional flow cross-section of the cylindrical flow diverter chamber of the diverter element comprises a diverter bump feature which provides a flow path cross-section perpendicular to the third principal axis that transitions from (b)(i) a circular cross-section of the third radial cross-sectional dimension at the first end of the cylindrical flow diverter chamber to (b)(ii) a semi-circular cross-section at the second end of the cylindrical flow diverter chamber that includes a partial third radial cross-sectional dimension for the first portion of the compound cross-section and a flat portion for the second portion of the compound cross-section. Still further, in one embodiment, the second radial cross-sectional dimension is equal to the first radial cross-sectional dimension.

In another embodiment, the third radial cross-sectional dimension is equal to the first radial cross-sectional dimension. The first, second and third radial cross-sectional dimensions are selected from among the group consisting of a circular radius and an elliptical radii. In addition, the flow diverter transition surface, as viewed in a direction of a cross-section of the second end of the cylindrical flow diverter chamber, includes an arc length of an edge at an intersection of the flow diverter transition surface with an inner surface of either the first conduit or the second conduit, wherein the edge of the arc length is included in an angle measured from a center of a flow geometry of either the first conduit or the second conduit, to an intersecting inside surface of the respective first conduit or the second conduit, from zero to one hundred and eight degrees.

In a further embodiment, the aerosol medicament delivery adapter includes wherein an area of the flow path cross-section at the second end of the cylindrical flow diverter chamber is less than an area of the flow path cross-section at the first end thereof, further wherein a ratio of the area at the second end to the area at the first end is greater than zero and less than one. In another embodiment, the second cross-section comprises a half-moon cross-section. In yet another embodiment, the second cross-section comprises a partial-moon cross-section.

According to another embodiment, a system for dispensing medicament into a ventilation circuit, comprises a pressure generating device configured to deliver pressurized air; a nebulizer for delivering an aerosolized medicament; a patient circuit, coupled to the pressure generating device and the nebulizer, for delivering a pressurized flow of air with aerosolized medicament to a patient interface, wherein the patient circuit includes the aerosol medicament delivery adapter.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

Figure 6:
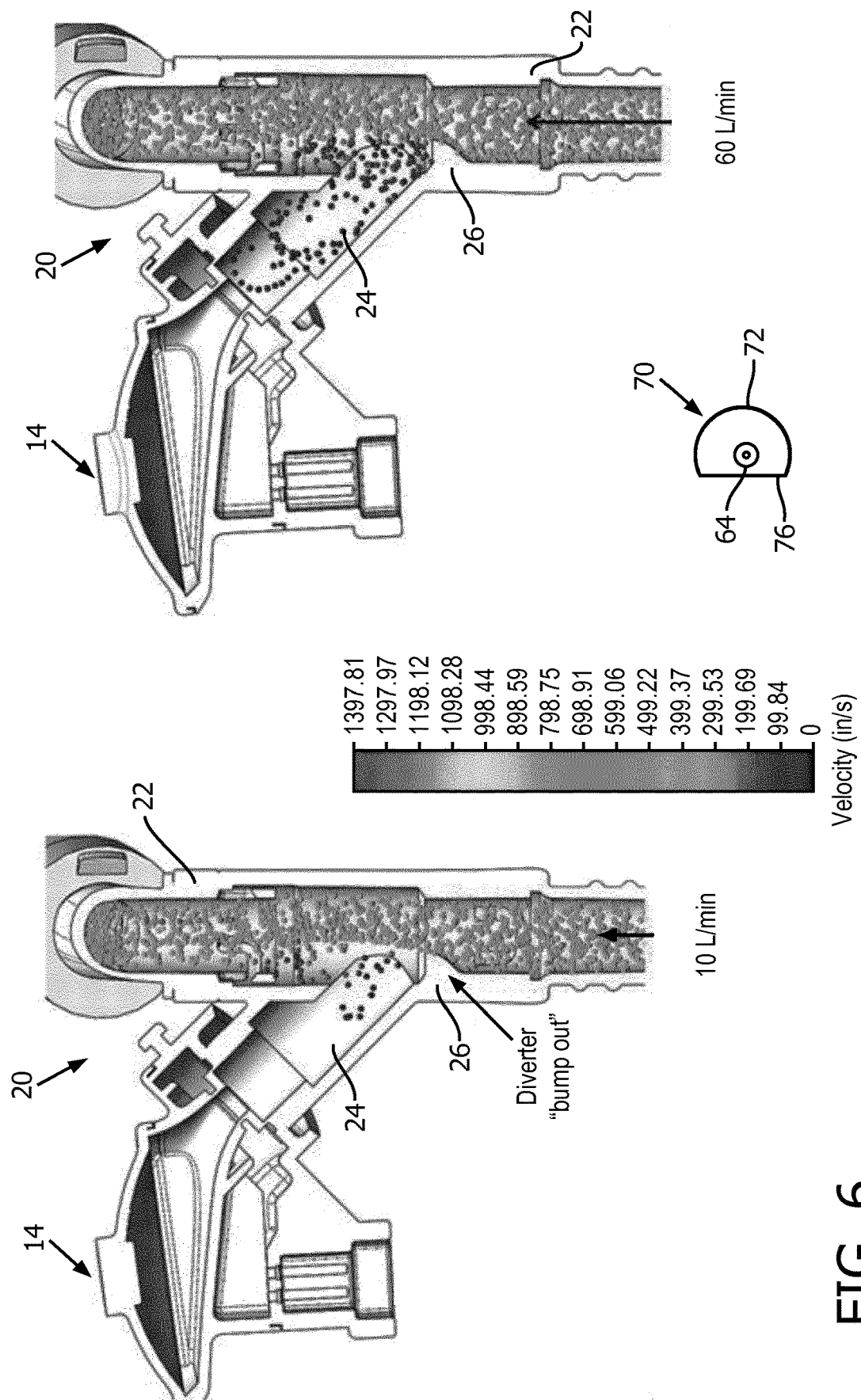
Figure 7:
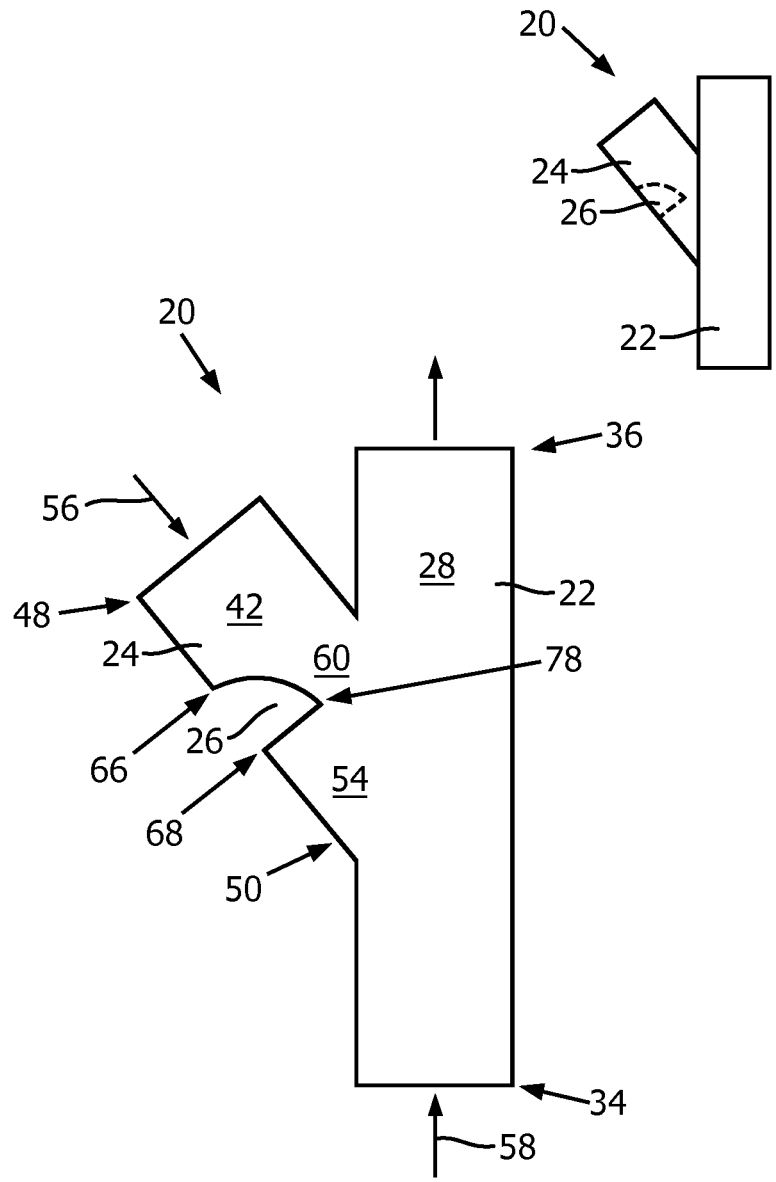

FIG. 6 is a perspective diagram view of an aerosol medicament delivery adapter and a representation of an entrainment of aerosol medicament particles using a pressurized gas flow of 10 L/min and 60 L/min according to an embodiment of the present disclosure; and FIG. 7 is a schematic cross-sectional view of an aerosol medicament delivery adapter according to another embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 1:
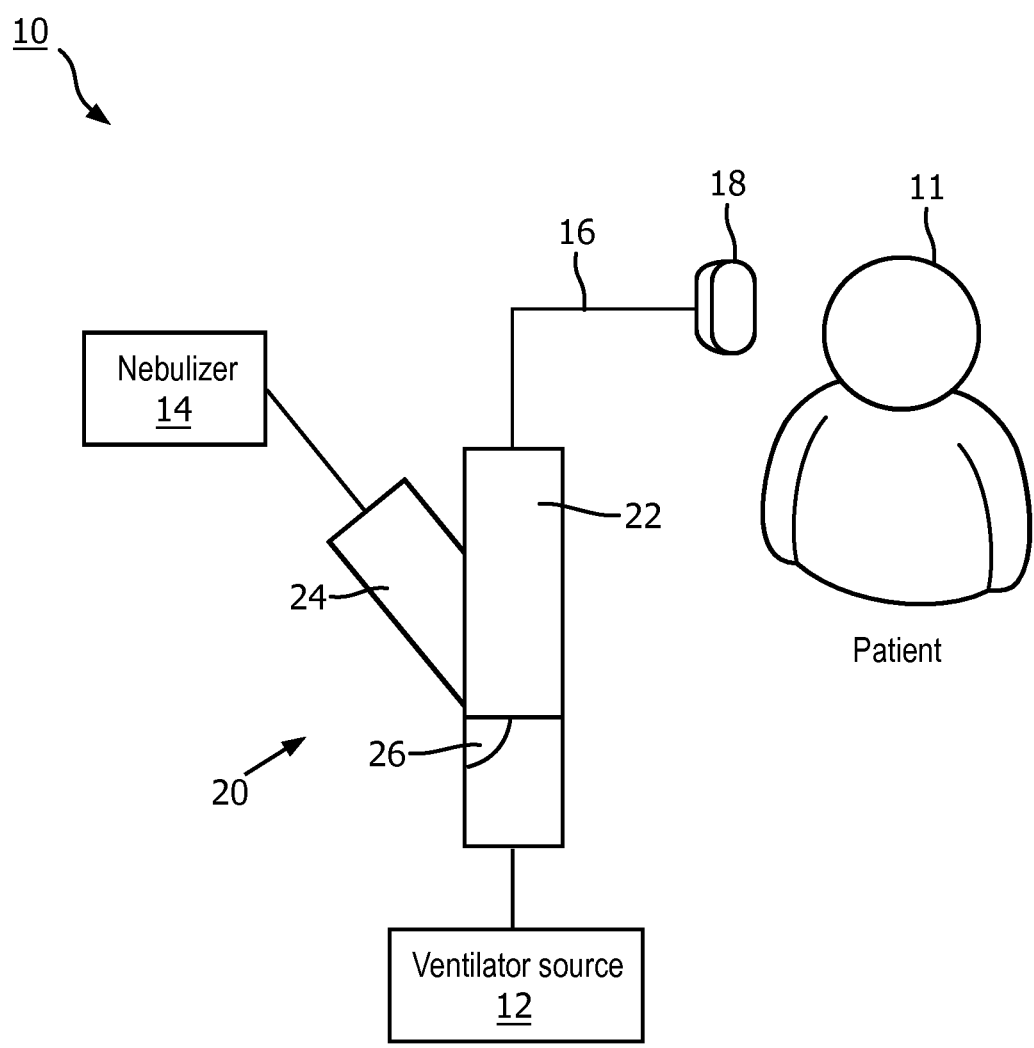
FIG. 1 is a block diagram view of a system for dispensing medicament into a patient circuit that includes an aerosol medicament delivery adapter according to an embodiment of the present disclosure.

With reference now to FIG. 1, a block diagram view of a system 10 for dispensing medicament into a patient circuit that includes an aerosol medicament delivery adapter according to an embodiment of the present disclosure is shown. The system 10 includes a ventilator source 12 configured to provide a flow of pressurized gas, a nebulizer or particle generator 14 configured to provide a source of aerosolized medicament particles, a patient circuit 16 the comprises suitable ventilation tubing, and a patient interface 18, such as a ventilation mask or the like. System 10 further includes an aerosol medicament delivery adapter 20, coupled between the ventilator source 12, nebulizer 14, and patient interface 18, within the patient circuit 16, as will be discussed further herein below. The aerosol medicament delivery adapter 20 includes a primary flow path conduit 22, an aerosol delivery conduit 24 and a diverter element 26.

In operation, system 10 for dispensing medicament into a ventilation circuit delivers a pressurized flow of gas, via the pressure generating device 12, into the primary flow path conduit 22 of the aerosol medicament delivery adapter 20. The nebulizer 14 delivers an aerosolized medicament into the aerosol delivery conduit 24 of the aerosol medicament delivery adaptor 20. The patient circuit 16, which is coupled to the pressure generating device 12 and the nebulizer 14 via the aerosol medicament delivery adapter 20, delivers a pressurized flow of air with aerosolized medicament to a patient 11, via the patient interface 18.

Figure 2:
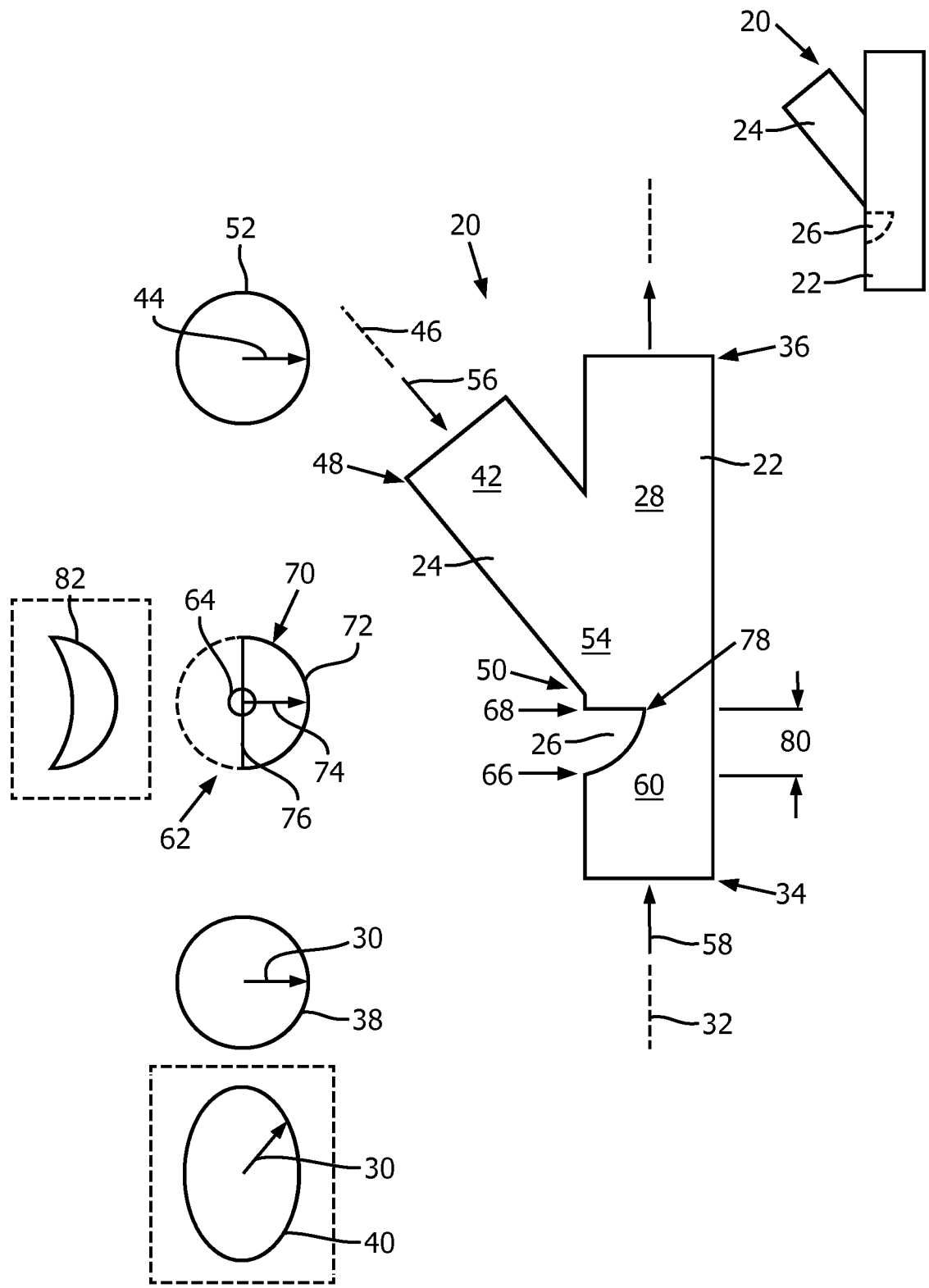
FIG. 2 is a schematic cross-sectional view of an aerosol medicament delivery adapter according to an embodiment of the present disclosure.

Turning now to FIG. 2, a schematic cross-sectional view of an aerosol medicament delivery adapter 20 according to an embodiment of the present disclosure is shown. In this embodiment, the first conduit 22, second conduit 24 and diverter element 26 are integrally formed with one another. The first conduit 22 comprises the primary flow path conduit enclosing a cylindrical flow path chamber 28 having (i) a first radial cross-sectional dimension 30 and (ii) a first principal axis 32, extending between a first end 34 that corresponds to an upstream end and a second end 36 that corresponds to a downstream end. In one embodiment, the first conduit 22 is a cylinder with a circular cross-section 38 and the first radial cross-sectional dimension 30 is a radius. In another embodiment, the first conduit 22 is a cylinder with an elliptical or oval cross-section 40 and the first radial cross-sectional dimension 30 is an elliptical radii.

The second conduit 24 comprises the aerosol medicament delivery conduit enclosing a cylindrical aerosol delivery chamber 42 having (i) a second radial cross-sectional dimension 44 and (ii) a second principal axis 46, extending between a first end 48 that corresponds to an upstream end and a second end 50 that corresponds to a downstream end of the second conduit 24. The first end 48 of the second conduit 24 is adapted to be fluidly coupled to a nebulizer or particle generator 14, such as shown in FIG. 1. In one embodiment, the second conduit 24 is a cylinder with a circular cross-section 52 and the second radial cross-sectional dimension 44 is a radius. In another embodiment, the second conduit 24 is a cylinder with an elliptical or oval cross-section (not shown) and the first radial cross-sectional dimension 44 is an elliptical radii.

The second end 50 of the second conduit 24 is fluidly coupled to the first conduit 22 at a Y-junction 54 proximate the first end 34 of the first conduit 22. In one embodiment, the Y-junction 54 comprises the second conduit or aerosol delivery conduit 24 being coupled to the first conduit or flow path conduit 22 such that the second principal axis 46 intersects the first principal axis 32 at an angle of less than 90 degrees. In another embodiment, the second principal axis 46 is angled with respect to the first principal axis 32 for enabling the second conduit 24 to have a downstream flow direction 56 of aerosolized delivery that opposes the downstream direction 58 of the pressurized gas flow.

With reference still to FIG. 2, the diverter element 26 comprises a cylindrical flow diverter chamber 60 disposed within the first conduit 22. The cylindrical flow diverter chamber 60 includes (i) a transitional flow cross-section 62 and (ii) a third principal axis 64, extending between a first end 66 and a second end 68 of the cylindrical flow diverter chamber 60. In this embodiment, the third principal axis 64 is aligned with the first principal axis 32. The transitional flow cross-section 62 of the cylindrical flow diverter chamber 60 includes a flow path cross-section perpendicular to the third principal axis 64 that transitions from (i) a first cross-section of a third radial cross-sectional dimension 30 at the first end 66 of the cylindrical flow diverter chamber 60 to (ii) a second cross-section that comprises a compound cross-section 70 that includes a first portion 72 with the third radial cross-section dimension 74 and a second portion 76 with a cross-sectional dimension determined by a flow diverter transition surface 78 at the second end 68 of the cylindrical flow diverter chamber 60. The diverter element 26, and thus the cylindrical flow diverter chamber 60, is also characterized by a length dimension 80 along the third principal axis 64. Furthermore, the transitional flow cross-section 62 includes a non-linear transition from the first end 66 to the second end 68 along the length dimension 80.

Referring still to FIG. 2, the second end 68 of the cylindrical flow diverter chamber 60 is fluidly coupled within the first conduit 22 proximate the first end 34 of the first conduit, upstream of the second conduit 24. In other words, while positioned within the first conduit 22, the flow diverter element 26 is just upstream of the particle generator at, or proximate to, the Y-junction. Specific size and location dimensions of the diverter element 26 can be determined according to the requirements of a given aerosol particle entrainment application. Responsive to a pressurized gas flow along a flow path within the first conduit 22 in a downstream direction 58, the diverter element 26 creates flow eddies for enhancing an entrainment of aerosol particles, delivered via the second conduit 24, within the pressurized gas flow along the flow path within the first conduit 22. In one embodiment, the second cross-section 70 comprises a cross-section with a half-moon shape, or half-moon shaped cross-section. In another embodiment, the second cross-section comprises a cross-section with a partial-moon shape or a partial-moon cross-section, indicated via reference numeral 82. In addition, an area of the flow path cross-section at the second end 68 of the cylindrical flow diverter chamber 60 is less than an area of the flow path cross-section at the first end 66 thereof, further wherein a ratio of the area at the second end 68 to the area at the first end 66 is greater than zero and less than one.

Referring still to FIG. 2, the flow diverter transition surface 78, as viewed in a direction of a cross-section of the second end 68 of the cylindrical flow diverter chamber 60, includes an arc length of an edge at an intersection of the flow diverter transition surface 78 with an inner surface of the first conduit 22. The edge of the arc length is included in an angle measured from a center of the flow geometry of the first conduit 22 to an intersecting inside surface of the first conduit 22, from zero to one hundred and eighty degrees.

In another embodiment, the transitional flow cross-section 62 of the cylindrical flow diverter chamber 60 of the diverter element 26 comprises a diverter bump feature which provides a flow path cross-section perpendicular to the third principal axis 64 that transitions from (i) a circular cross-section of the third radial cross-sectional dimension 74 at the first end 66 of the cylindrical flow diverter chamber 60 to (ii) a semi-circular cross-section at the second end 68 of the cylindrical flow diverter chamber 60 that includes a partial third radial cross-sectional dimension for the first portion 72 of the compound cross-section and a flat portion for the second portion 76 of the compound cross-section.

In one embodiment, the second radial cross-sectional dimension 44 is equal to the first radial cross-sectional dimension 30. In another embodiment, the third radial cross-sectional dimension 74 is equal to the first radial cross-sectional dimension 30. Still further, in another embodiment, the first, second and third radial cross-sectional dimensions are selected from among the group consisting of a circular radius and an elliptical radii.

Figure 3:
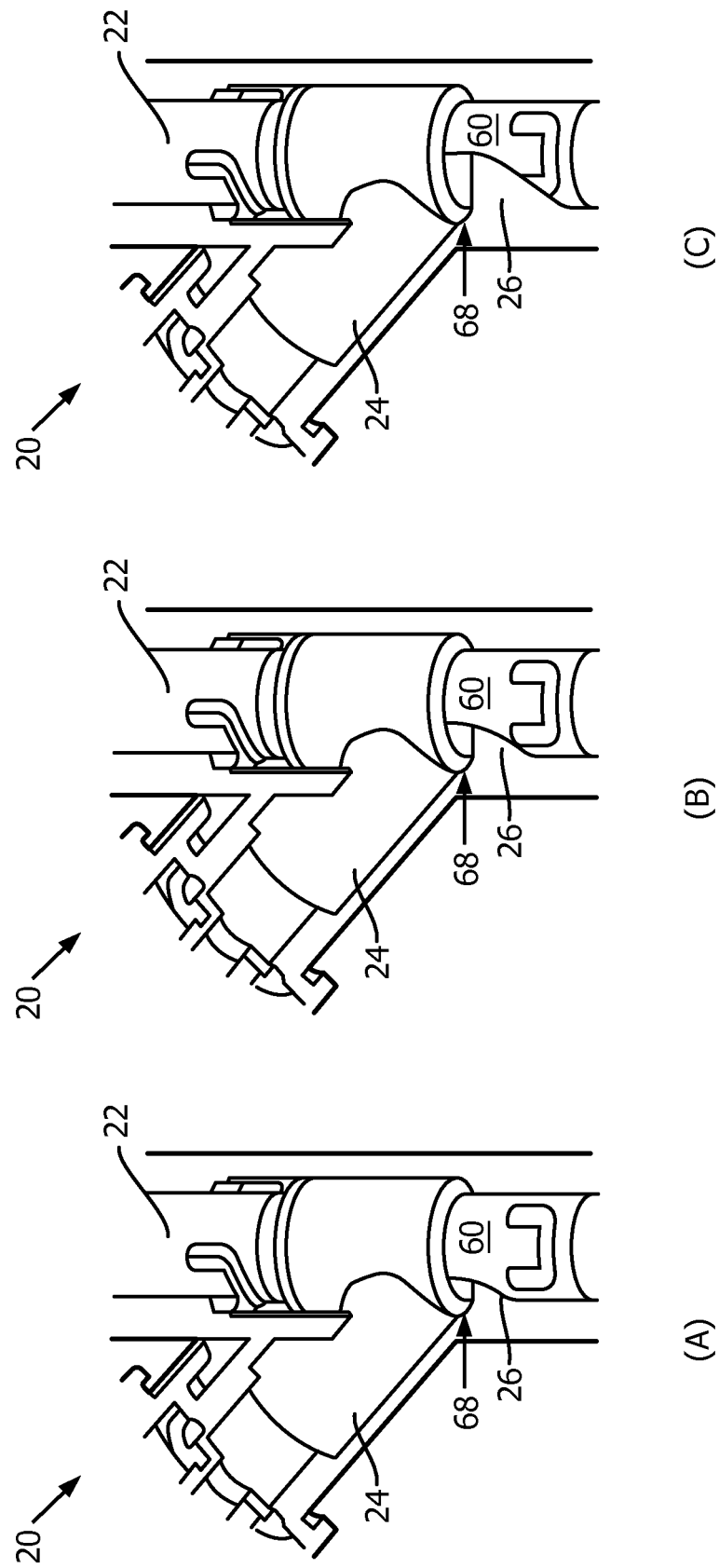
FIG. 3 is a perspective diagram view of an aerosol medicament delivery adapter with a diverter element of various sizes according to an embodiment of the present disclosure.

Referring now to FIG. 3, a perspective diagram view of an aerosol medicament delivery adapter with a diverter element of various sizes according to an embodiment of the present disclosure is shown. In the embodiments of FIG. 3, the second cross-section 70 (see FIG. 2) at the second end 68 of the cylindrical flow diverter chamber 60 comprises a semi-circular cross-section, wherein the first portion 72 includes the partial third radial cross-sectional dimension 74 and wherein the second portion 76 includes a flat portion determined by the flow diverter transition surface 78. In addition, the transitional flow cross-section 62 at the second end 68 of the cylindrical flow diverter chamber 60 comprises one selected from the group consisting of (i) a small diverter that corresponds with the semi-circular cross-section at the second end of the cylindrical flow diverter chamber being at least 90% of a circular cross-section at the first end of the cylindrical flow diverter chamber as shown in FIG. 3(A), (ii) a medium diverter that corresponds with the semi-circular cross-section at the second end of the cylindrical flow diverter chamber being at least 75%, but less than 90% of the circular cross-section at the first end of the cylindrical flow diverter chamber as shown in FIG. 3(B), and (iii) a large diverter that corresponds with the semi-circular cross-section at the second end of the cylindrical flow diverter chamber being at least 50%, but less than 75%, of the circular cross-section at the first end of the cylindrical flow diverter chamber as shown in FIG. 3(C).

Figure 4:
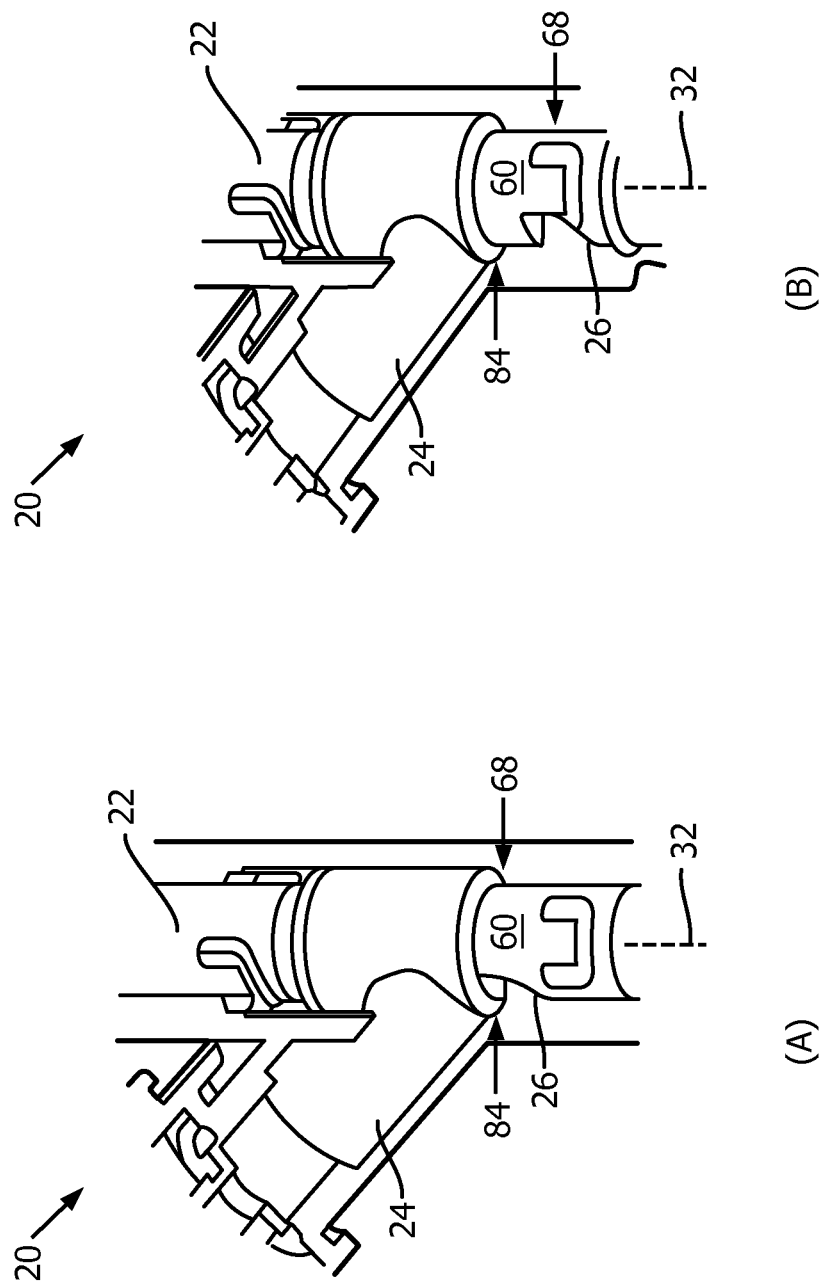
FIG. 4 is a perspective diagram view of an aerosol medicament delivery adapter with various dimensional spacing along a principal axis according to an embodiment of the present disclosure.

With reference now to FIG. 4, a perspective diagram view of an aerosol medicament delivery adapter with various dimensional spacing along a principal axis according to an embodiment of the present disclosure is shown. In one embodiment, the second end 68 of the cylindrical flow diverter chamber 60 is located upstream within the first conduit 22, and further the second end 68 of the cylindrical flow diverter chamber 60 is spaced along the principal axis 32 (FIG. 2) by a distance of up to 20 mm from a position 84 within the first conduit 22 where the second conduit 24 intersects with the first conduit 22.

Figure 5:
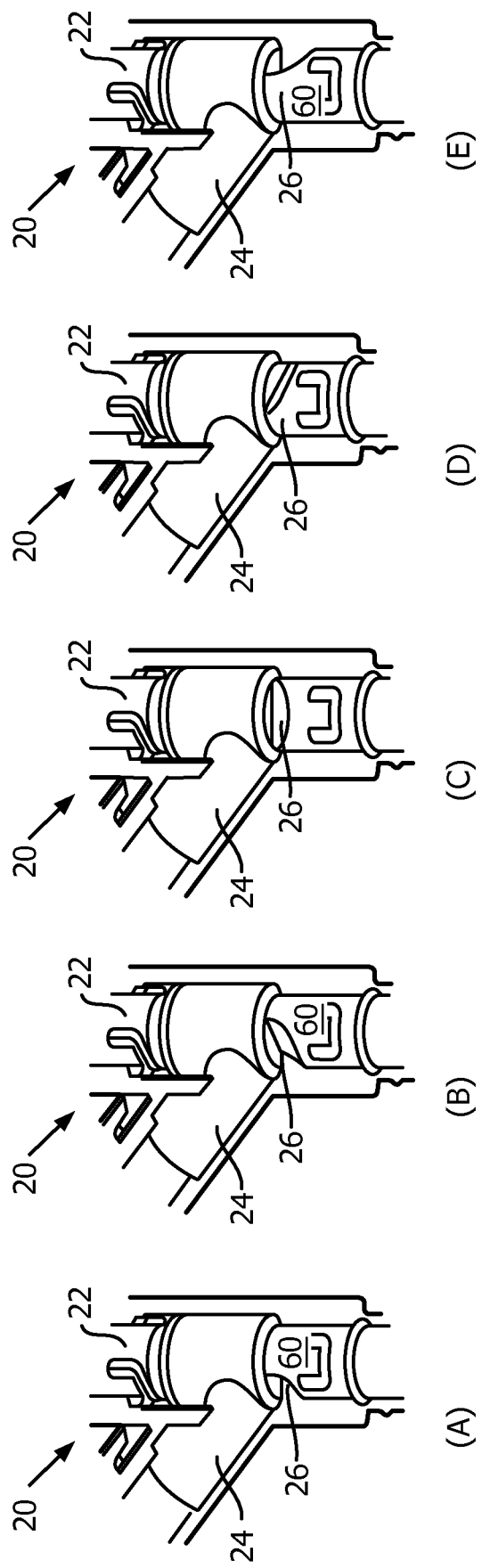
FIG. 5 is a perspective diagram view of an aerosol medicament delivery adapter in various orientations according to an embodiment of the present disclosure.

Turning now to FIG. 5, a perspective diagram view of an aerosol medicament delivery adapter 20 in various orientations according to an embodiment of the present disclosure is shown. With respect to the illustrations in FIG. 5, the first principal axis 32 and the second principal axis 46 are disposed in a plane (e.g., in the plane of the page). In addition, the second portion 76 (see FIG. 2) of the compound cross-section 62 is one selected from the group consisting of (a) oriented at an angle parallel to the plane (as illustrated by FIG. 5(C)) and (b) rotated out of parallel with the plane at an angle within a range of −90 to +90 degrees with respect to the plane. For example, FIG. 5(A) illustrates the second portion 76 of the compound cross-section 62 being rotated out of parallel with the plane at an angle of −90 degrees with respect to the plane. FIG. 5(B) illustrates the second portion 76 of the compound cross-section 62 being rotated out of parallel with the plane at an angle of −45 degrees with respect to the plane. FIG. 5(D) illustrates the second portion 76 of the compound cross-section 62 being rotated out of parallel with the plane at an angle of +45 degrees with respect to the plane. Similarly, FIG. 5(E) illustrates the second portion 76 of the compound cross-section 62 being rotated out of parallel with the plane at an angle of +90 degrees with respect to the plane.

With reference still to FIG. 5, in another embodiment, the cylindrical flow diverter chamber 60 is rotatable about the third principal axis 64 (FIG. 2) for disposing the second portion 76 of the compound cross-section 62 in one or more angles within the range of −90 to +90 degrees with respect to the plane.

With reference now to FIG. 6, a perspective diagram view of an aerosol medicament delivery adapter 20 and a representation of an entrainment of aerosol medicament particles using a pressurized gas flow of 10 L/min and 60 L/min according to an embodiment of the present disclosure is shown. In particular, an entrainment of aerosolized particles delivered from the nebulizer 14, via the second conduit, within the pressurized gas flow along the flow path within the first conduit 22 with the diverter element 26 are shown. In addition, the entrainment of particles is further significantly increased in response to a change in pressurized gas flow increasing from 10 L/min to 60 L/min. The illustration of FIG. 6 includes the aerosol medicament delivery adapter 20 of FIGS. 3(B) and 5(A), as discussed herein above.

Turning now to FIG. 7, a schematic cross-sectional view of an aerosol medicament delivery adapter according to another embodiment of the present disclosure is shown. The embodiment of FIG. 7 is similar to the embodiments discussed herein above, with the following differences. The diverter element 26 comprises a cylindrical flow diverter chamber 60 disposed within the second conduit 24. The second end of the cylindrical flow diverter chamber 60 is fluidly coupled within the second conduit 24 downstream of the nebulizer or particle generator 14 at, or proximate to, the Y-junction 54. In addition, while positioned within the second conduit 24, the flow diverter element 26 is just downstream of the particle generator at, or proximate to, the Y-junction. Specific size and location dimensions of the diverter element 26 can be determined according to the requirements of a given aerosol particle entrainment application. In addition, the second end 50 of the aerosol delivery conduit 24 is coupled to the first conduit or flow path conduit 22 nearer to the first end 34 of the flow path conduit 22 than to the second end 36 of the flow path conduit 22.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in any ventilation therapy method or device in which aerosolized medication delivery is used in conjunction with the therapy. In addition, the flow paths can have variable cross-sectional footprint. For example, the diverter element could be configured to change in cross-sectional footprint within the flow stream in response to flow rate changes. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An aerosol medicament delivery adapter comprising:
a first conduit that comprises a flow path conduit enclosing a cylindrical flow path chamber having (i) a first radial cross-sectional dimension and (ii) a first principal extending between a first end that corresponds to an upstream end and a second end that corresponds to a downstream end;
a second conduit that comprises an aerosol medicament delivery conduit enclosing a cylindrical aerosol delivery chamber having (i) a second radial cross-sectional dimension and (ii) a second principal axis, extending between a first end that corresponds to an upstream end and a second end that corresponds to a downstream end of the second conduit, wherein the first end of the second conduit is adapted to be fluidly coupled to a nebulizer and wherein the second end of the second conduit is fluidly coupled to the first conduit at a Y-junction proximate the first end of the first conduit; and
a diverter element that comprises a cylindrical flow diverter chamber disposed within at least one of the first conduit and the second conduit, wherein the cylindrical flow diverter chamber includes (a)(i) a transitional flow cross-section and (a)(ii) a third principal axis extending between a first end and a second end of the cylindrical flow diverter chamber, wherein the transitional flow cross-section of the cylindrical flow diverter chamber includes a flow path cross-section perpendicular to the third principal axis that transitions from (b)(i) a first cross-section of a third radial cross-sectional dimension at the first end of the cylindrical flow diverter chamber to (b)(ii) a second cross-section that comprises a compound cross-section that includes a first portion with the third radial cross-section dimension and a second portion with a cross-sectional dimension determined by a flow diverter transition surface at the second end of the cylindrical flow diverter chamber, wherein the second end of the cylindrical flow diverter chamber is fluidly coupled (c)(i) within the first conduit proximate the first end of the first conduit, upstream of the second conduit or (c)(ii) within the second conduit downstream of the nebulizer at, or proximate to, the Y-junction, wherein responsive to a pressurized gas flow along a flow path within the first conduit in a downstream direction, the diverter element creates flow eddies for enhancing an entrainment of aerosol particles, delivered via the second conduit, within the pressurized gas flow along the flow path within the first conduit.

2. The aerosol medicament delivery adapter according to claim 1, wherein the second cross-section at the second end of the cylindrical flow diverter chamber comprises a semi-circular cross-section, wherein the first portion includes the partial third radial cross-sectional dimension and wherein the second portion includes a flat portion determined by the flow diverter transition surface, further wherein the transitional flow cross-section at the second end of the cylindrical flow diverter chamber comprises one selected from the group consisting of (i) a small diverter that corresponds with the semi-circular cross-section at the second end of the cylindrical flow diverter chamber being at least 90% of a circular cross-section at the first end of the cylindrical flow diverter chamber, (ii) a medium diverter that corresponds with the semi-circular cross-section at the second end of the cylindrical flow diverter chamber being at least 75%, but less than 90% of the circular cross-section at the first end of the cylindrical flow diverter chamber, and (iii) a large diverter that corresponds with the semi-circular cross-section at the second end of the cylindrical flow diverter chamber being at least 50%, but less than 75%, of the circular cross-section at the first end of the cylindrical flow diverter chamber.

3. The aerosol medicament delivery adapter according to claim 1, wherein the first principal axis and the second principal axis are disposed in a plane, and wherein the second portion of the compound cross-section is one selected from the group consisting of (a) oriented at an angle parallel to the plane and (b) rotated out of parallel with the plane at an angle within a range of −90 to +90 degrees with respect to the plane.

4. The aerosol medicament delivery adapter according to claim 3, further wherein the cylindrical flow diverter chamber is rotatable about the third principal axis for disposing the second portion of the compound cross-section in one or more angles within the range of −90 to +90 degrees with respect to the plane.

5. The aerosol medicament delivery adapter according to claim 1, further wherein the third principal axis is aligned with one selected from the group consisting of the first principal axis and the second principal axis.

6. The aerosol medicament delivery adapter according to claim 1, further wherein second end of the cylindrical flow diverter chamber is located upstream within the first conduit, and further wherein the second end of the cylindrical flow diverter chamber is spaced by a distance of up to 20 mm from a position within the first conduit where the second conduit intersects with the first conduit.

7. The aerosol medicament delivery adapter according to claim 1, wherein the Y-junction comprises the second conduit being coupled to the first conduit such that the second principal axis intersects the first principal axis at an angle of less than 90 degrees.

8. The aerosol medicament delivery adapter according to claim 7, further wherein the second principal axis is angled with respect to the first principal axis for enabling the second conduit to have a downstream flow direction of aerosolized delivery that opposes the downstream direction of the pressurized gas flow.

9. The aerosol medicament delivery adapter according to claim 1, wherein the second end of the aerosol delivery conduit is coupled to the flow path conduit nearer to the first end of the flow path conduit than to the second end of the flow path conduit.

10. The aerosol medicament delivery adapter according to claim 1, wherein the transitional flow cross-section of the cylindrical flow diverter chamber of the diverter element comprises a diverter bump feature which provides a flow path cross-section perpendicular to the third principal axis that transitions from (b)(i) a circular cross-section of the third radial cross-sectional dimension at the first end of the cylindrical flow diverter chamber to (b)(ii) a semi-circular cross-section at the second end of the cylindrical flow diverter chamber that includes a partial third radial cross-sectional dimension for the first portion of the compound cross-section and a flat portion for the second portion of the compound cross-section.

11. The aerosol medicament delivery adapter according to claim 1, wherein the third radial cross-sectional dimension is equal to the first radial cross-sectional dimension.

12. The aerosol medicament delivery adapter according to claim 1, wherein the first, second and third radial cross-sectional dimensions are selected from among the group consisting of a circular radius and an elliptical radii.

13. The aerosol medicament delivery adapter according to claim 1, wherein the flow diverter transition surface as viewed in a direction of a cross-section of the second end of the cylindrical flow diverter chamber, includes an arc length of an edge at an intersection of the flow diverter transition surface with an inner surface of either the first conduit or the second conduit, wherein the edge of the arc length is included in an angle measured from a center of a flow geometry of either the first conduit or the second conduit, to an intersecting inside surface of the respective first conduit or the second conduit, from zero to one hundred and eight degrees.

14. The aerosol medicament delivery adapter according to claim 1, wherein an area of the flow path cross-section at the second end of the cylindrical flow diverter chamber is less than an area of the flow path cross-section at the first end thereof, further wherein a ratio of the area at the second end to the area at the first end is greater than zero and less than one.

15. A system for dispensing medicament into a ventilation circuit, comprising:
 a pressure generating device configured to deliver pressurized air;
 a nebulizer for delivering an aerosolized medicament;
 a patient circuit coupled to the pressure generating device and the nebulizer for delivering a pressurized flow of air with aerosolized medicament to a patient interface wherein the patient circuit the aerosol medicament delivery adapter according to claim 1.

* * * * *